United States Patent [19]
Dani et al.

[11] Patent Number: 6,025,172
[45] Date of Patent: Feb. 15, 2000

[54] ISOLATION AND SEQUENCING OF THE HAZEL FAD2-NGENE

[75] Inventors: Maria Dani, Sala Di Caserta; Sergio Catello, Naples, both of Italy

[73] Assignee: Soremartec S.A., Belgium

[21] Appl. No.: 08/811,177

[22] Filed: Mar. 4, 1997

[30] Foreign Application Priority Data

Mar. 4, 1996 [CH] Switzerland ............................. 0550/96

[51] Int. Cl.[7] ............................. C12N 9/02; C07H 21/04
[52] U.S. Cl. ........................ 435/189; 435/41; 435/252.3; 435/320.1; 435/325; 435/419; 514/44; 536/23.2
[58] Field of Search ........................ 435/41, 189, 252.3, 435/320.1, 325, 419; 536/23.2; 514/44

[56] References Cited

PUBLICATIONS

Okuley et al.; The Plant Cell, vol. 6, 147–158, Jan. 1994; "Arabidopsis FAD2 Gene Encodes the Enzyme That Is Essential for Polyunsaturated Lipid Synthesis".

Smith et al.; Nature, vol. 334, 724–726, Aug. 1998; "Antisense RNA inhibition of polygalacturonase gene expression in transgenic tomatoes".

Flavell; Proc. Natl. Acad. Sci. USA, vol. 91, 3490–3496, Apr. 1994; "Inactivation of gene expression in plants as a consequence of specific sequence duplication".

Verwoerd et al.; Nucleic Acids Research, vol. 17, No. 6, 2362, 1989; "A small–scale procedure for the rapid isolation of plant RNAs".

Valenta et al. "Homology of the major birch–pollen allergen, Bet v I, with the major pollen allergens of alder, hazel, and hornbeam at the nucleic acid level as determined by cross–hybridization." Journal of Allergy and Clinical Immunology (Mar. 1991).

*Primary Examiner*—Robert A. Wax
*Attorney, Agent, or Firm*—Rothwell, Figg, Ernst & Kurz, P.C.

[57] ABSTRACT

The invention relates to the isolation from hazel (*Corylus avellana* L.) of the FAD2-N gene coding for the Δ12 desaturase enzyme of the microsomal fraction and, in particular, provides the nucleotide sequence and the deduced amino-acid sequence of the gene and provides for the use of the FAD2-N gene as a probe for the isolation of other plant desaturases. The invention also relates to the use of the FAD2-N gene for altering desaturase levels and consequently the fatty-acid composition of the plant.

9 Claims, 13 Drawing Sheets

FIG. 2A

```
CCTCATAAAAAGTAAGCTCATTTACCTCAAGTAGGGTTTCCTTATGACAAATGAGTCCC      60
GGAGTATTTTTCATTCGAGTAAATGGAGTTCATCCCAAAGGAATACTGTTACTCAGGG

GCAATCCTTTCTATGAGGTGCTATAATTGCAAATGTCCAAATCATAGGGATATGGATCC     120
CGTTAGGAAAGATACTCCACGATATTAACGTTTACAGGTTTAGTATCCCTATACCTAGG

AAATACTATTAATATTATGTAGTGTGTTTTTTTTTTCCCTCAAATTACTCTCACACCT     180
TTTATGATAATTATATACATCACACAAAAAAAAGGGAGTTTAAATGAGAGTGTGGA

AAGTTGATTTCTCCAGCATTGGACATAGCCTCTGTAGACAATGGGAGCTAGAAGCCGAA     240
TTCAACTAAAAGAGGTCGTAACCCTGTATCGGAGACATCGTTACCCTCGATCTTCGGCTT
                                          MetGlyAlaArgSerArg

TGCCTGCTACCAACAAGCCTAAAGAGCAAAAAACACCCAGCGAGCACCACACACAA       300
ACGGACGATGGTTGTTCGGATTCTCGTTTTTTGTGGGTAGGTCGCTCGTGGTGTGTT
MetProAlaThrAsnLysProLysGluGlnLysThrProIleGlnArgAlaProHisThr

AACCCCCATTCACTCTTAGCCAACTCAAGAAAGCCGTCCCACCCAATTGTTCCAACGCT     360
TTGGGGGTAAGTGAGAATCGGTTGAGTTCTTCGGCAGGGTGGGTTAACAAGGTTGCGA
LysProProPheThrLeuSerGlnLeuLysLysAlaValProProAsnCysPheGlnArg

CTCTCCTACGCTCGTTCTCATATGTGTTTATGACCTCTCCTTAGCCTTCCTCTTCTACT     420
GAGAGGATGCGAGCAAGAGTATACACAAATACTGGAGGAATCGGAAGGAGAAGATGA
SerLeuArgSerPheSerTyrValValTyrAspLeuSerLeuAlaPheLeuPheTyr
```

FIG. 2B

```
ATATTGCTACCCTCTTACTTCCATCTCCTCCCTCACCCCCTTTCCTACTTGGCATGGTCAA    480
TATAACGATGGAGAATGAAGGTAGAGAGGGAGGAGTGGGGGAAAGGATGAACCGTACCAGTT
TyrIleAlaThrSerTyrPheHisLeuLeuProHisProLeuSerTyrLeuAlaTrpSer

TCTATTGGGCTCTCCAAGGCTGCATTCTCCACGGCGTTTGGTCATCGCACACATGAGTGCG    540
AGATAACCCGAGAGGTTCCGACGTAAGAGTGGCCGCAAACCAGTAGCGTGTACTCACGC
IleTyrTrpAlaLeuGlnGlyCysIleLeuThrGlyValIleAlaHisGluCys

GTCACCATGCCTTTAGTGACTACCAATGGTTGATGACATGGTTGGCCTAACCCTTCACT    600
CAGTGGTACGGAAATCACTGATGGTTACCCAACTACTGTACCAACCGGATTGGGAAGTGA
GlyHisAlaPheSerAspTyrGlnTrpValAspMetValGlyLeuThrLeuHis

CTGCTCTTTTAGTTCCATACTTTTCATGGAAGATTAGCCACTGTCGCCACTCTAACA    660
GACGAGAAAATCAAGGTATGAAAAGTACCTTCTAATCGGTGACAGCGGTGGTGAGATTGT
SerAlaLeuLeuValProTyrPheSerTrpLysIleSerHisCysArgHisSerAsn

CCGGCTCCCCTTGACCGAGATGAGGTGTTGTCCCCAAGCCGAAATCCAAAATGCCATGGT    720
GGCCGAGGGAACTGGCTCTACTCCACAAACAGGGTTCGGCTTTAGGTTTTACGGTACCA
ThrGlySerLeuAspArgAspGluValPheValProLysProLysSerLysMetProTrp

TTTCTAAGTACTTCAACAACCACCAGGTAGGGTCCTCACTCTCTTTGATCACACTCACTC    780
AAAGATTCATGAAGTTGTTGGGTGGTCCATCCCAGGAGTGAGAAAACTAGTGTGAGTGAG
PheSerLysTyrPheAsnAsnProProGlyArgValLeuThrLeuLeuIleThrLeuThr

TAGGCTGGCCCTTGTACTTAGCCTTGAATGTTTCTGGCCGACCCTATGATCGTTTTGCTT    840
ATCCGACCGGGAACATGAATCGGAACTTACAAAGACCGGCTGGGATACTAGCAAAACGAA
LeuGlyTrpProLeuTyrLeuAlaLeuAsnValSerGlyArgProTyrAspArgPheAla
```

FIG. 2C

```
GCCACTATGATCCCTATGGCCCCATTTATTCCAATCGCGAAAGGTGTCAAATATTTGTCT    900
CGGTGATACTAGGGATACCGGGGTAAATAAGGTTAGCGCTTTCCACAGTTTATAAACAGA
CysHisTyrAspProTyrGlyProIleTyrSerAsnArgGluArgCysGlnIlePheVal

CGGATGCTGGTGTCTTTGCTACAACTTATGTGCTTTACGCAGCAATGTCAAAAGGGC      960
GCCTACGACCACAGAACGATGTTGAATACACGAAATGATGCGTCGTTACAGTTTTCCCG
SerAspAlaGlyValPheAlaThrThrTyrValLeuTyrTyrAlaAlaMetSerLysGly

TGGCATGGCTTGTATTCATTTATGGTATGCCATTGCTCATAGTGAATGGCTTCCTTGTAT    1020
ACCGTACCGAACATATAGTAAATACCATACGGTAACGAGTATCACTTACCGAAGGAACATA
LeuAlaTrpLeuValPheIleTyrGlyMetProLeuLeuIleValAsnGlyPheLeuVal

TAATCACCTACTTGCAGCACACTCACCCTGCATTGCCGCACTATGACTCATCAGAATGG    1080
ATTAGTGGATGAACGTCGTGTGAGTGGGACGTAACGGCGTGATACTGAGTAGTCTTACCC
LeuIleThrTyrLeuGlnHisThrProHisThrProAlaLeuProHisTyrAspSerSerGluTrp

ATTGGCTTAGGGGGGCATTGGCGACGGCGGATAGAGATTACGGAATGCTGAATAAGGTTT    1140
TAACCGAATCCCCCCGTAACCGCTGCCGCCTATCTCTAATGCCTTACGACTTATTCCAAA
AspTrpLeuArgGlyAlaLeuAlaThrAlaLeuAlaAspArgAspTyrGlyMetLeuAsnLysVal

TCCACAATATCATAGACACCCATGTGCTCCACCATCTCTTCTCTACCATGCCTCATTACC    1200
AGGTGTTATAGTATCTGTGGGTACACCGAGTGGTAGAGAAGATGGTACGGAGTAATGG
PheHisAsnIleIleAspThrHisValAlaHisHisLeuPheSerThrMetProHisTyr

ATGCAAATGGAAGCCACCAAAGCACCAAGTCAATCAAGTCAAATACTACCAGTTTGATG    1260
TACGTTTACCTTCGGTGGTTTCGTTAGTTCAGTTATAACCCGTTTATGATGGTCAAACTAC
HisAlaMetGluAlaThrLysAlaIleLysSerIleLeuGlyLysTyrGlnPheAsp
```

FIG. 2D

```
GCACTCCAGTTTACAAGGCAGTGTGGAGGAGGCTAAAGAGTGCCTTTATGTTGAGTCGG          1320
CGTGAGGTCAAATGTTCCGTCACACCTCCCTCCGATTTCTCACGGAAATACAACTCAGCC
GlyThrProValTyrLysAlaValTrpArgGluAlaLysGluCysLeuTyrValGluSer

ACGAGGGGGCCCCTAACAAAGGTGTTTTCTGGTATCAGAGCAAGCTGTGATATTGGCTGG         1380
TGCTCCCCCGGGATTGTTTCCACAAAGACCATAGTCTCGTTCGACACTATAACCGACC
AspGluGlyAlaProAsnLysGlyValPheTrpTyrGlnSerLysLeu

ATAGAGCCAAAGAAAATGTGATTAGTAAGGTAGTGTCTTTGGTCAGTTTGGTGTGTTAAG         1440
TATCTCGGTTTCTTTTACACTAATCATTCCATCACAGAAACCAGTCAAACCACACAATTC

GAACAAATAATAATTAGCGACTATGAATAGTTATTGTTAAACAAAATTCACCCTTAT           1500
CTTGTTTATTATTAATCGCTGATACTTATCAATAACAATTGTTTTAAGTGGAATA

GTTTAGCAGGAACTTTTCTGGCTACACTTTTTTTCGTATGAAAAGCGCATATTTTTAAT         1560
CAAATCGTCCTTGAAAAGACCGATGTGAAAAAAAGCATACTTTTCGCGTATAAAAAATTA

TGTTATATTGTTTGACATTACTCAAGCTTCAAAATTAATATCACAGAAAATATCCAATG         1620
ACAATATAACAAAACTGTAATGAGTTCGAAGTTTTAATTATAGTGTCTTTTATAGGTTAC

TCGAAGGTTTCATTGTAGGTTGAAACTTTATATTGAGGTGG                            1662
AGCTTCCAAAGTAACATCCAACTTTTGAAATATAACTCCACC
```

FIG. 3

```
tccaacgctctctcctacgctcgttctcatatgttgtttatgacctctcc    50
ttagccttcctcttctactatattgctacctcttacttccatctcctccc   100
tcaccccttcctacttggcatggtcaatctattgggctctccaaggct     150
gcattctcaccggcgtttgggtcatcgcacatgagtgcggtcaccatgcc   200
tttagtgactaccaatgggttgatgacatggttggcctaaccttcactc    250
tgctcttttagttccatactttcatggaagattagccactgtcgccacc    300
actctaacaccggctcccttgaccgagatgaggtgtttgtcccaagccg    350
aaatccaaaatgccatggttttctaagtacttcaacaacccaccaggtag   400
ggtcctcactcttttgatcacactcactctaggctggcccttgtacttag   450
ccttgaatgtttctggccgaccctatgatcgttttgcttgccactatgat   500
ccctatggccccatttattccaatcgcgaaaggtgtcaaatatttgtctc   550
ggatgctggtgtctttgctacaacttatgtgctttactacgcagcaatgt   600
caaaagggctggcatggcttgtattcatttatggtatgccattgctcata   650
gtgaatggcttccttgtattaatcacctacttgcagcacactcaccctgc   700
attgccgcactatgactcatcagaatgggattggcttaggggggcattgg   750
cgacggcggatagagattacggaatgctgaataaggttttccacaatatc   800
atagacaccatgtggctcaccatctcttctaccatgcctcattacca     850
tgcaatggaagccaccaaagcaatcaagtcaatattgggcaaatactacc   900
agtttgatggcactccagtttacaaggcagtgtggagggaggctaaagag   950
tgcctttatgttgagtcggacgagggggcccctaacaaaggtgttttctg  1000
gtatcagagcaagctgtgatattggctggatagagccaaagaaaatgtga  1050
ttagtaaggtagtgtctttggtcagtttggtgtgttaaggaacaaataat  1100
ataattagcgactatgaatagttattgttaaa 1133
```

FIG. 4A

| | | |
|---|---|---|
| 1 | ---------------------------------------- | I. SEQ |
| 1 | CCTCATAAAAAGTAAGCTCATTTACCTCAAGTAGGGTTT | N2.SEQ |
| 1 | ---------------------------------------- | I. SEQ |
| 41 | CCTTATGACAAATGAGTCCCGCAATCCTTTTCTATGAGGT | N2.SEQ |
| 1 | ---------------------------------------- | I. SEQ |
| 81 | GCTATAATTGCAAATGTCCAAATCATAGGGATATGGATCC | N2.SEQ |
| 1 | ---------------------------------------- | I. SEQ |
| 121 | AAATACTATTAATATTATGTAGTGTGTTTTTTTTTTCCC | N2.SEQ |
| 1 | ---------------------------------------- | I. SEQ |
| 161 | TCAAATTTACTCTCACACCTAAGTTGATTTTCTCCAGCAT | N2.SEQ |
| 1 | ---------------------------------------- | I. SEQ |
| 201 | TGGACATAGCCTCTGTAGACAATGGGAGCTAGAAGCCGAA | N2.SEQ |
| 1 | ---------------------------------------- | I. SEQ |
| 241 | TGCCTGCTACCAACAAGCCTAAAGAGCAAAAAACACCCAT | N2.SEQ |
| 1 | ---------------------------------------- | I. SEQ |
| 281 | CCAGCGAGCACCACACACAAAACCCCCATTCACTCTTAGC | N2.SEQ |
| 1 | ---------------------------------------- | I. SEQ |
| 321 | CAACTCAAGAAAGCCGTCCCACCCAATTGTTTCCAACGCT | N2.SEQ |
| 10 | CTCTCCTACGCTCGTTCTCATATGTTGTTTATGACCTCTC | I. SEQ |
| 361 | CTCTCCTACGCTCGTTCTCATATGTTGTTTATGACCTCTC | N2.SEQ |
| 50 | CTTAGCCTTCCTCTTCTACTATATTGCTACCTCTTACTTC | I. SEQ |
| 401 | CTTAGCCTTCCTCTTCTACTATATTGCTACCTCTTACTTC | N2.SEQ |
| 90 | CATCTCCTCCCTCACCCCCTTTCCTACTTGGCATGGTCAA | I. SEQ |
| 441 | CATCTCCTCCCTCACCCCCTTTCCTACTTGGCATGGTCAA | N2.SEQ |
| 130 | TCTATTGGGCTCTCCAAGGCTGCATTCTCACCGGCGTTTG | I. SEQ |
| 481 | TCTATTGGGCTCTCCAAGGCTGCATTCTCACCGGCGTTTG | N2.SEQ |

FIG. 4B

| | | |
|---|---|---|
| 170 | GGTCATCGCACATGAGTGCGGTCACCATGCCTTTAGTGAC | I.SEQ |
| 521 | GGTCATCGCACATGAGTGCGGTCACCATGCCTTTAGTGAC | N2.SEQ |
| 210 | TACCAATGGGTTGATGACATGGTTGGCCTAACCCTTCACT | I.SEQ |
| 561 | TACCAATGGGTTGATGACATGGTTGGCCTAACCCTTCACT | N2.SEQ |
| 250 | CTGCTCTTTTAGTTCCATACTTTTCATGGAAGATTAGCCA | I.SEQ |
| 601 | CTGCTCTTTTAGTTCCATACTTTTCATGGAAGATTAGCCA | N2.SEQ |
| 290 | CTGTCCCCACCACTCTAACACCGGCTCCCTTGACCGAGAT | I.SEQ |
| 641 | CTGTCGCCACCACTCTAACACCGGCTCCCTTGACCGAGAT | N2.SEQ |
| 330 | GAGGTGTTTGTCCCCAAGCCGAAATCCAAAATGCCATGGT | I.SEQ |
| 681 | GAGGTGTTTGTCCCCAAGCCGAAATCCAAAATGCCATGGT | N2.SEQ |
| 370 | TTTCTAAGTACTTCAACAACCCACCAGGTAGGGTCCTCAC | I.SEQ |
| 721 | TTTCTAAGTACTTCAACAACCCACCAGGTAGGGTCCTCAC | N2.SEQ |
| 410 | TCTTTTGATCACACTCACTCTAGGCTGGCCCTTGTACTTA | I.SEQ |
| 761 | TCTTTTGATCACACTCACTCTAGGCTGGCCCTTGTACTTA | N2.SEQ |
| 450 | GCCTTGAATGTTTCTGGCCGACCCTATGATCGTTTTGCTT | I.SEQ |
| 801 | GCCTTGAATGTTTCTGGCCGACCCTATGATCGTTTTGCTT | N2.SEQ |
| 490 | GCCACTATGATCCCTATGGCCCCATTTATTCCAATCGCGA | I.SEQ |
| 841 | GCCACTATGATCCCTATGGCCCCATTTATTCCAATCGCGA | N2.SEQ |
| 530 | AAGGTGTCAAATATTTGTCTCGGATGCTGGTGTCTTTGCT | I.SEQ |
| 881 | AAGGTGTCAAATATTTGTCTCGGATGCTGGTGTCTTTGCT | N2.SEQ |
| 570 | ACAACTTATGTGCTTTACTACGCAGCAATGTCAAAAGGGC | I.SEQ |
| 921 | ACAACTTATGTGCTTTACTACGCAGCAATGTCAAAAGGGC | N2.SEQ |
| 610 | TGGCATGGCTTGTATTCATTTATGGTATGCCATTGCTCAT | I.SEQ |
| 961 | TGGCATGGCTTGTATTCATTTATGGTATGCCATTGCTCAT | N2.SEQ |

FIG. 4C

```
650   AGTGAATGGCTTCCTTGTATTAATCACCTACTTGCAGCAC    I. SEQ
1001  AGTGAATGGCTTCCTTGTATTAATCACCTACTTGCAGCAC    N2.SEQ

690   ACTCACCCTGCATTGCCGCACTATGACTCATCAGAATGGG    I. SEQ
1041  ACTCACCCTGCATTGCCGCACTATGACTCATCAGAATGGG    N2.SEQ

730   ATTGGCTTAGGGGGGCATTGGCGACGGCGGATAGAGATTA    I. SEQ
1081  ATTGGCTTAGGGGGGCATTGGCGACGGCGGATAGAGATTA    N2.SEQ

770   CGGAATGCTGAATAAGGTTTTCCACAATATCATAGACACC    I. SEQ
1121  CGGAATGCTGAATAAGGTTTTCCACAATATCATAGACACC    N2.SEQ

810   CATGTGGCTCACCATCTCTTCTCTACCATGCCTCATTACC    I. SEQ
1161  CATGTGGCTCACCATCTCTTCTCTACCATGCCTCATTACC    N2.SEQ

850   ATGCAATGGAAGCCACCAAAGCAATCAAGTCAATATTGGG    I. SEQ
1201  ATGCAATGGAAGCCACCAAAGCAATCAAGTCAATATTGGG    N2.SEQ

890   CAAATACTACCAGTTTGATGGCACTCCAGTTTACAAGGCA    I. SEQ
1241  CAAATACTACCAGTTTGATGGCACTCCAGTTTACAAGGCA    N2.SEQ

930   GTGTGGAGGGAGGCTAAAGAGTGCCTTTATGTTGAGTCGG    I. SEQ
1281  GTGTGGAGGGAGGCTAAAGAGTGCCTTTATGTTGAGTCGG    N2.SEQ

970   ACGAGGGGGCCCCTAACAAAGGTGTTTTCTGGTATCAGAG    I. SEQ
1321  ACGAGGGGGCCCCTAACAAAGGTGTTTTCTGGTATCAGAG    N2.SEQ

1010  CAAGCTGTGATATTGGCTGGATAGAGCCAAAGAAAATGTG    I. SEQ
1361  CAAGCTGTGATATTGGCTGGATAGAGCCAAAGAAAATGTG    N2.SEQ

1050  ATTAGTAAGGTAGTGTCTTTGGTCAGTTTGGTGTGTTAAG    I. SEQ
1401  ATTAGTAAGGTAGTGTCTTTGGTCAGTTTGGTGTGTTAAG    N2.SEQ

1090  GAACAAATAATAATAATTAGCGACTATGAATAGTTATTGT    I. SEQ
1441  GAACAAATAATAATAATTAGCGACTATGAATAGTTATTGT    N2.SEQ
```

FIG. 4D

```
1130 TAAA                                                I. SEQ
1481 TAAACAAAATTCACCCTTATGTTTAGCAGGAACTTTTCTG            N2.SEQ

1133                                                     I. SEQ
1521 GCTACACTTTTTTTCGTATGAAAAGCGCATATTTTTAAT             N2.SEQ

1133                                                     I. SEQ
1561 TGTTATATTGTTTTGACATTACTCAAGCTTCAAAATTAAT            N2.SEQ

1133                                                     I. SEQ
1601 ATCACAGAAAATATCCAATGTCGAAGGTTTCATTGTAGGT            N2.SEQ

1133                                                     I. SEQ
1641 TGAAAACTTTATATTGAGGTGG                              N2.SEQ
```

FIG. 5

```
  1  MGARSRMP-ATNKPKEQKTPIQRAPHTKPPFTLSQLKKAV        N2.PRO
  1  MGAGGRTDVPPANRKSEVDPLKRVPFEKPQFSLSQIKKAI        L43921.PRO
  1  MGAGGRMPVPTSSKKSETDTTKRVPCEKPPFSVGDLKKAI        L26296.PRO

40  PPNCFQRSLLRSFSYVVYDLSIAFLFYYIATSYFHLLPHP        N2.PRO
 41  PPHCFQRSVLRSFSYVVYDLTIAFCLYYVATHYFHLLPGP        L43921.PRO
 41  PPHCFKRSIPRSFSYLISDIIIASCFYYVATNYFSLLPQP        L26296.PRO

80  LSYLAWSIYWALQGCILTGVWVIAHECGHHAFSDYQWDD         N2.PRO
 81  LSFRGMAIYWAVQGCILTGVWVIAHECGHHAFSDYQLLDD        L43921.PRO
 81  LSYLAWPLYWACQGCVLTGIWVIAHECGHHAFSDYQWLDD        L26296.PRO

120  MVGLTLHSALLVPYFSWKISHCRHHSNTGSLDRDEVFVPK        N2.PRO
121  IVGLILHSALLVPYFSWKYSHRRHHSNTGSLERDEVFVPK        L43921.PRO
121  TVGLIFHSFLLVPYFSWKYSHRRHHSNTGSLERDEVFVPK        L26296.PRO

160  PKSKMEWFSKYFNNPPGRVLTLLITLTLGWPLYLALNVSG        N2.PRO
161  QKSCIKWYSKYLNNPPGRVLTLAVTLTLGWPLYLALNVSG        L43921.PRO
161  QKSAIKWYGKYLNNHLGRIMMLTVQFVLGWPLYLAFNVSG        L26296.PRO

200  RPYDRFACHYDPYGPIYSNRERCQIFVSDAGVFATTYMLY        N2.PRO
201  RPYDRFACHYDPYGPIYSDRERLQIYISDAGVLAVVYGLF        L43921.PRO
201  RPYDGFACHFFPNAPIYNDRERLQIYLSDAGILAVCFGLY        L26296.PRO

240  YAAMSKGLAWLVFIYGMPLLIVNGFLVLITYLQHTHPALP        N2.PRO
241  RLAMAKGLAWVVCVYGVPLLMVNGFLVLITFLQHTHPALP        L43921.PRO
241  RYAAAQGMASMICLYGVPLLIVNAFLVLITYLQHTHFSLP        L26296.PRO

280  HYDSSEWDWLRGALATADRDYGMLNKVFHNIIDTHVAHHL        N2.PRO
281  HYTSSEWDWLRGALATVDRDYGILNKVFHNITDTHVAHHL        L43921.PRO
281  HYDSSEWDWLRGALATVDRDYGILNKVFHNITDTHVAHHL        L26296.PRO

320  FSTMPHYHAMEATKAIKSILGKYYQFDGTPVYKAVWREAK        N2.PRO
321  FSTMPHYHAMEATKAIKPILGEYYRFDETPFVKAMWREAR        L43921.PRO
321  FSTMPHYNAMEATKAIKPILGDYYQFDGTPWYVAMYREAK        L26296.PRO

360  ECLYVESDEGAPNKGVFWYQSKL                         N2.PRO
361  ECIYVEPDQSTESKGVFWYNNKL                         L43921.PRO
361  ECIYVEPDREGDKKGVYWYNNKL                         L26296.PRO
```

ISOLATION AND SEQUENCING OF THE HAZEL FAD2-N GENE

The present invention relates to the isolation from hazel (*Corylus avellana* L.) of the FAD2-N gene which codes for the Δ12 desaturase enzyme of the microsomal fraction.

More particularly, the invention relates to nucleic acids comprising the nucleotide sequence of the FAD-N gene, the derived amino-acid sequence of the gene, and the use as of the gene a probe for the isolation of other plant desaturases. The invention also relates to the use of this gene for altering the desaturase levels, and consequently the fatty-acid composition of the plant. The invention further relates to recombinant DNA molecules comprising the FAD2-N gene, host organisms comprising these DNA molecules, the hazel Δ12 desaturase enzyme encoded by the FAD2-N gene, and fusion polypeptides comprising the enzyme. Host organisms include vegetable cells, animal cells and micro-organisms. In the fusion polypeptides of the invention, amino acids added to the polypeptide should not interfere with the activity of the encoded desaturase, or if so, can be easily removed from the polypeptide.

Alteration of the fatty-acid composition may have various applications in the industrial field. One of the greatest problems with hazelnuts is that they become rancid by oxidation. This is due to the auto-oxidation of unsaturated lipids with the consequent formation of volatile substances with a rancid odour which cannot easily be eliminated by the usual preservation systems. Amongst the possible strategies for reducing the tendency to become rancid, the best seems to be that of reducing the degree of unsaturation of the fatty acids present in the kernel oil, since susceptibility to auto-oxidation is positively correlated with this parameter. In fact, the rate of peroxide formation is correlated with the number of C=C double bonds in the fatty acids. The rate of auto-oxidation of the fatty acids in comparison with the oleate (18:1) is about 30 times greater in the linoleate (18:2) and 80 times greater in the linolenate (18:3). Moreover, the volatile substances resulting from the degradation of the linoleate and of the linolenate have a lower threshold of perception than those derived from the oleate. A reduction in linoleic acid should reduce the availability of substrates for lipoxygenase, reduce the loss of vitamin E during preservation, and reduce the production of volatile substances such as hexanals.

In the angiosperms, most of the synthesis of polyunsaturated lipids takes place by means of a single enzyme, that is, Δ12 (or ω6) desaturase (18:1 desaturase), of the endoplasmic reticulum, although there is an 18:1 chloroplast desaturase in the leaves of some plants. Moreover, this enzyme is responsible for more than 90% of the synthesis of polyunsaturated fatty acids in non-photosynthetic tissues such as, for example, in the kernels. The conversion of oleic acid (18:1) to linoleic acid (18:2) thus takes place by means of Δ12 desaturase, and from linoleic acid to linolenic acid (18:3) by means of Δ15 (or ω3) desaturase.

It has been shown with mutants of Arabidopsis that the FAD2 locus contains a gene which codes for the oleate desaturase enzyme of the endoplasmic reticulum (Okuley et al, 1994, The Plant Cell 6, 147–158). The FAD2 gene was in fact able to complement mutants of Arabidopsis which were deficient in desaturase activity of the endoplasmic reticulum. The gene coding for the same enzyme in soya has also recently been isolated and sequenced (Heppard et al, 1995, Plant Physiol., in press).

A reduction in the Δ12 desaturase levels should therefore lead to a reduction in the linoleic acid content and, as a secondary effect, probably also to a reduction in linolenic acid. In hazelnuts the percentage of linoleic acid varies from 5 to 15%; the percentage of linolenic acid is from 0.1 to 0.2%. A reduction in these fatty acids should therefore be useful in the preservation of hazelnuts. There is therefore clearly a need to isolate the gene which codes for the Δ12 desaturase of the endoplasmic reticulum. The sequence of the gene could thus be used for gene inactivation in hazelnut kernels. This inactivation could be carried out either by the antisense technique (Smith et al. (1988) Nature 334, 724–726) or by the "transwitch" technique (Flavell (1994) Proc. Natl. Acad. Sci. USA 91, 3490–3496). In the antisense technique, the hazel would have to be transformed by the entire FAD2-N gene or by portions thereof, inserted in the opposite direction to the regulating sequences. In the "transwitch" technique, the hazel would have to be transformed by an identical copy of the FAD2-N gene. The present invention also relates to nucleic acids encoding a protein or polypeptide having an amino acid homology of at least about 80% to the amino acid sequence of the hazel Δ12 desaturase enzyme of the endoplasmic reticulum [SEQ ID NO:2] and having the function of the enzyme.

The subjects of the present invention are defined by the following claims.

Embodiments of the present invention will now be described with reference to the following drawings, in which:

FIG. 2 (SEQ ID NO:1) shows the nucleotide sequence of the hazel FAD2-N gene; the amino-acid sequence of the coding portion is also shown (SEQ ID NO:2);

FIG. 3 (SEQ ID NO:3) shows the nucleotide sequence of the "I" clone of cDNA,

Figure 6:
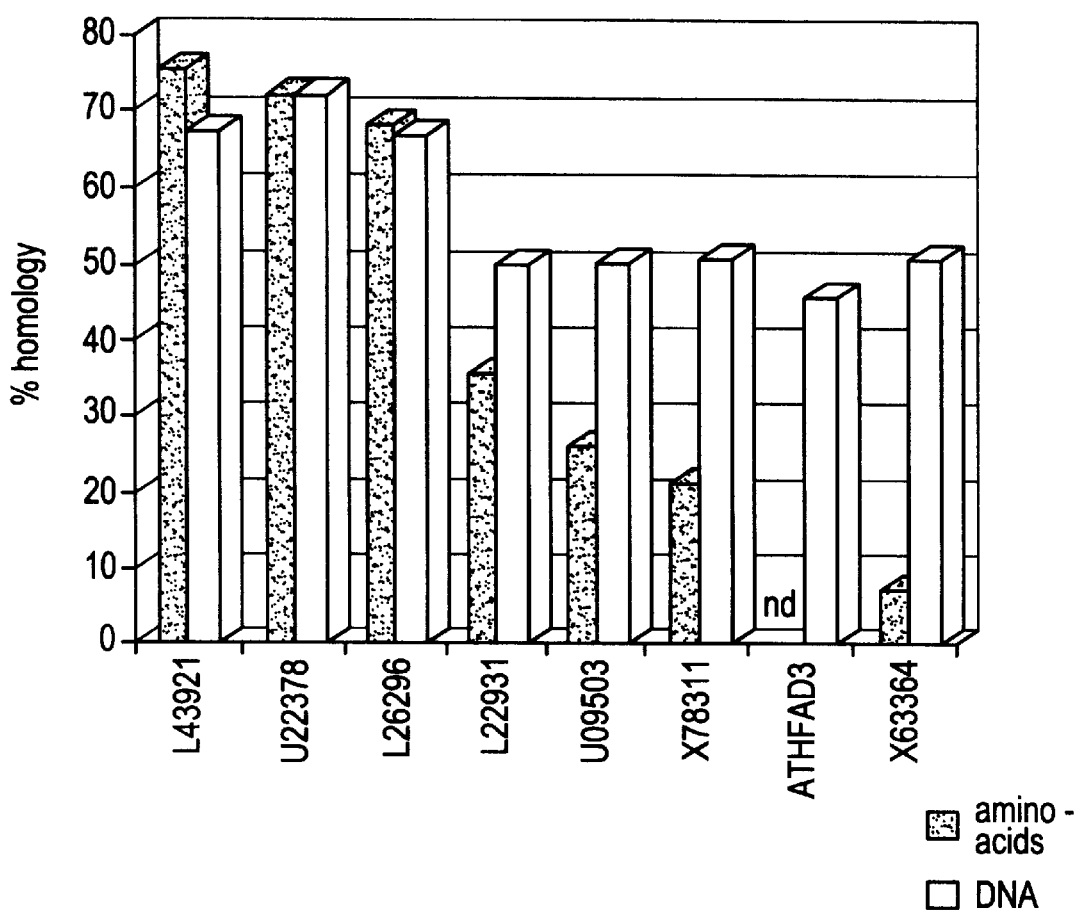
Figure 7:
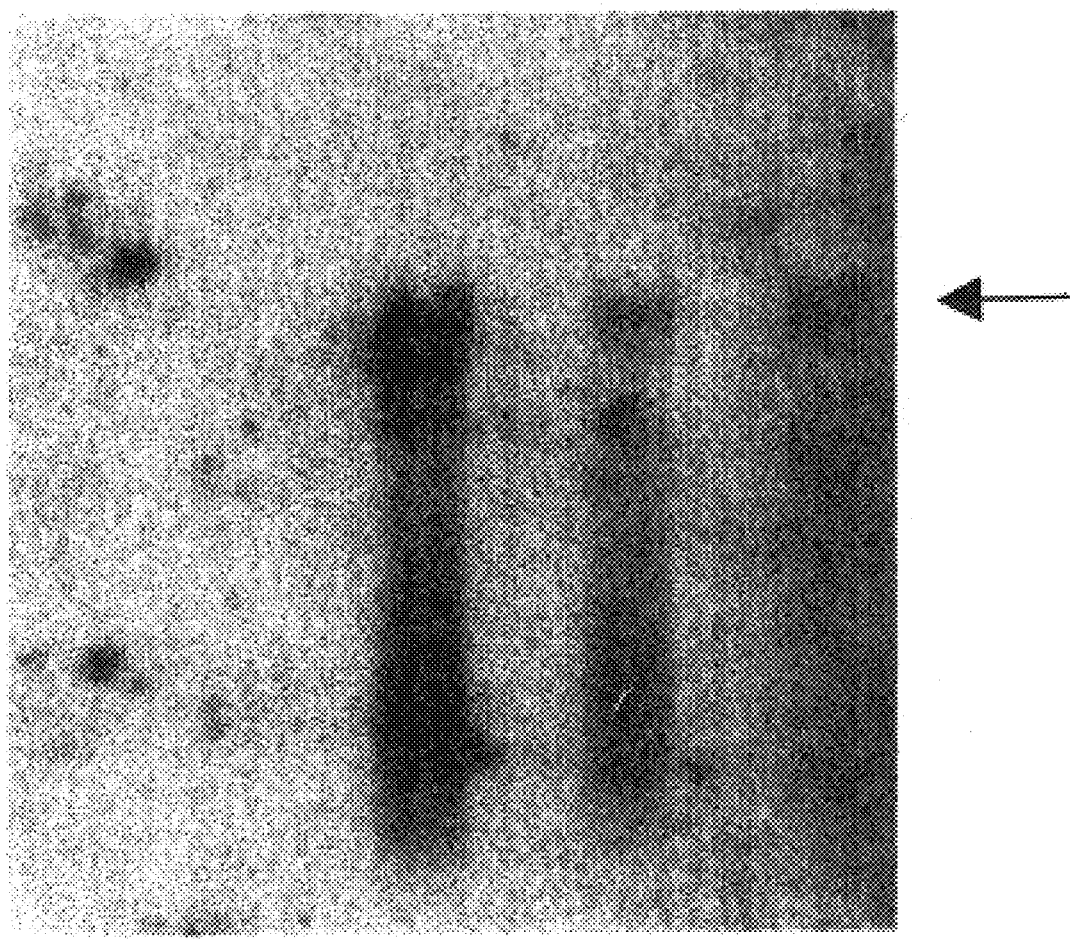

FIG. 4 shows a comparison between the nucleotide sequences of the "I" (SEQ ID NO:3) and "N2" (SEQ ID NO:1) clones, FIG. 5 shows a comparison between the amino acid of the Δ12 desaturases from hazelnut, Arabidopsis and soya, FIG. 6 shows the homology between hazel Δ12 desaturase and various desaturases of other plants, both plastid and of the endoplasmic reticulum, FIG. 7 shows the expression of the N2 gene in various varieties of hazel, both in the leaves and in the kernels.

ISOLATION AND CLONING OF THE FAD2 GENE OF *ARABIDOPSIS THALIANA* FOR USE AS A PROBE

In order to isolate the gene which codes for hazel Δ12 desaturase enzyme, it was necessary to use the FAD2 gene of Arabidopsis as a probe.

In order to isolate the Arabidopsis gene, two oligonucleotides were used as "primers" for the amplification of the sequences included between the start and the end of the gene. The oligonucleotides used were NOCC1 (SEQ ID NO:4) (CTGAATTCCAGGTGGAAGAATGCC) which contains the Eco RI restriction site and the sequences corresponding to the portion between bases 100 and 116 of the gene (Okuley J. et al, 1994, The Plant Cell 6, 147–158) and NOCC4 (AGGAATTCGACAATTTCTTCACCATCATGC) (SEQ ID NO:5) which contains the restriction site of the Eco RI enzyme and the sequences complementary to the portion between base 1245 and base 1266. The amplification reaction was as follows: 12.8 μl $H_2O$, 2.5 μl 10×PCR buffer (Perkin Elmer), 2.5 μl Arabidopsis genome DNA(10 ng/l), 1 μl dNTP, each 2.5 mM, 2 μl 25 mM $MgCl_2$, 1 μl NOCC1 oligonucleotide (SEQ ID NO:4) (50 ng/µl), 1 µl NOCC4 oligonucleotide (SEQ ID NO:5) (50 ng/µl) 0.2 µl Taq I DNA polymerase (Perkin Elmer) (5 U/µl). The mixture thus prepared was subjected to 1 denaturing cycle for 1 minute at 94° C. and to 40 cycles composed as follows: 30 seconds at 94° C., 1 minute at 52° C., 2 minutes at 72° C. The amplification products were separated on 1% agarose gel in TAE buffer (0.04M Tris-acetate, 0.002M EDTA) and stained with ethidium bromide at a concentration of 0.5 µg/ml. The portion of gel containing the fragment of the expected length was withdrawn. In order to extract the DNA, 10 µl of Qiaex resin (Qiaex extraction kit, firm Qiagen) were added for each 200 mg of gel. The supplier's method was then followed. The DNA was then supplemented with a tenth of a volume of 10×H buffer (Boehringer) and 20 units of Eco RI enzyme (Boehringer). After incubation overnight at 37° C., the DNA was precipitated with 0.1 volumes of 5M $NH_4OAc$ and one volume of isopropanol. After 10 minutes at ambient temperature, the DNA was centrifuged for 20 minutes at 14000 rpm and the precipitate was washed with 70% ethanol. The DNA was resuspended in 15 µl of $H_2O$. The concentration was determined on gel by comparison with a known standard.

The amplified fragment was inserted in the pUC18 vector. A ligation mixture was prepared as follows: 1 µl pUC18 plasmid DNA cut with Eco RI (20 ng), 1.5 µl fragment amplified with NOCC1 (SEQ ID NO:4) and 4 (25 ng), 1 µl 10× ligase buffer (Boehringer), 1 µl T4 DNA ligase (1 U/µl) (Boehringer), 4.5 µl $H_2O$. The reaction mixture was incubated at 14° C. for 12 hours.

In order to prepare competent cells, the method based on the compound hexamino-cobalt chloride was used (Maniatis, Molecular cloning, 1989, Cold Spring Harbor Laboratory Press, 1.76–1.81). 10 µl of the ligation mixture were added to each aliquot of competent cells, defrosted on ice. After the cells had been incubated on ice for 30 minutes they were subjected to thermal shock at 42° C. for 90 seconds and were then replaced in ice for 60 seconds. After the addition of 0.5 ml of SOC broth (2% Bactotryptone, 0.5% yeast extract, 10 mM NaCl, 2.5 mM KCl, 10 mM $MgCl_2$, 20 mM glucose, pH7), the cells were incubated at 37° C. with stirring for 90'. 100, 200 and 300 µl aliquots were spread on plates containing solid LB broth (10 gr/l NaCl, 10 gr/l Bactotryptone, 5 gr/l yeast extract, pH7.5, 15 gr/l agar) with the addition of 50 µg/ml of ampicillin and in the presence of IPTG and X-Gal. The plates were then incubated at 37° C. overnight.

Some of the bacterial colonies obtained were first analyzed for their plasmid content by a quick method (Maniatis, Molecular cloning, 1989, Cold Spring Harbor Laboratory Press, 1.32). The colonies containing a plasmid of the expected length were grown and their plasmid DNA extracted (Maniatis, Molecular cloning, 1989, Cold Spring Harbor Laboratory Press, 1.33). Those containing a fragment of the expected length (1160 bp) were identified by digestion of the plasmid DNA with Eco RI. The E1 colony was selected.

One end of the insert of the E1 colony was sequenced. The plasmid DNA of the E1 clone was denatured and partially sequenced by Sanger's method using the enzyme Sequenase and $^{35}$S-dATP (Amersham). The sequencing products were separated on 8% acrylamide, 8M urea, 1 ×TBE gel. After electrophoresis, the gel was dried and exposed overnight in contact with an autoradiographic plate (β max, Amersham). The sequence was compared with that published and was identical, identifying the Arabidopsis FAD2 gene in the cloned fragment.

Extraction of Nucleic Acids from Hazel

Hazelnuts of the Nocchione, Montebello and San Giovanni varieties were harvested when almost fully ripe. The kernel was skinned before being used or frozen in liquid nitrogen. The leaves were harvested at a young stage and frozen in liquid nitrogen. 3 ml of extraction buffer were used for each gram of vegetable material with the use of the method described by Verwoerd et al. (Nucl. Ac. Res., 1989, 2362). Upon completion of the extraction, two selective precipitations were carried out by the addition of NaCl 2M, and 2 volumes of 95% ethanol to eliminate polysaccharides. The final pellet was resuspended in $H_2O$. Further centrifuging was then carried out to eliminate any non-resuspended material.

DNA also was extracted from young leaves of the Nocchione and Montebello varieties. The vegetable tissue was pulverized in liquid nitrogen and the DNA extracted by the CTAB (REF) method. To eliminate the polysaccharides, NaCl 2M and 2 volumes of 95% ethanol were added. The samples were incubated for 15' at −80° C. and centrifuged for 15' at 4° C. and 14000 RPM (Eppendorf). This selective precipitation was repeated twice and the final pellet was resuspended in $H_2O$. Further centrifuging was then carried out to eliminate any non-resuspended material.

Checking of the Probe on Hazel DNA and RNA

About 20 µg of DNA of the Montebello and Nocchione varieties was cut with Eco RI restriction enzyme in a volume of 300 µl in the presence of 400 units of enzyme and H buffer (Promega), with incubation for one night at 37° C. After digestion had been checked by gel electrophoresis of one twentieth of the reaction mixture, the samples were precipitated with ethanol and resuspended in 30 µl of $H_2O$. The DNA was then subjected to electrophoresis on 0.7% agarose gel and transferred by capillarity onto nylon membrane (Southern blot) for one night in the presence of 20×SSC (3M NaCl, 0.3M Na citrate). The membrane was dried in air for 30' and then fixed by UV treatment (120,000 µJ/cm$^2$).

The Arabidopsis Δ12 desaturase gene was used as a probe. For this purpose, the plasmid DNA of the E1 clone (5 µg) was cut with 20 units of Eco RI in the presence of H buffer (Boehringer) in a volume of 30 µl for 12 hours at 37° C. The insert of the clone was separated from the vector by electrophoresis on 1% agarose gel and extracted from the gel with the use of Qiaex resin in accordance with the suppliers' instructions (Qiagen). The DNA was denatured for 10' at 100° C., cooled rapidly in dry ice, and marked by the random priming method with the use of 6000 Ci/mmol ($α^{32}$)P dATP and the reagents of Boehringer's marking kit.

The nylon membrane containing the hazel DNA was prehybridized for 1.5 hours at 55° C. in standard buffer (5×SSC, 0.1% (w/v) N-laurylsarcosine, 0.02% SDS, 1% blocking reagent solution) (10% blocking reagent solution: 10 gr Boehringer blocking reagent in 150 mM NaCl, 100 mM maleic acid, pH7.5). The membrane was then hybridized with the Arabidopsis probe for one night at 55° C. The non-hybridized probe was washed twice for 15' in 2×SSC, 0.1% SDS and twice for 15' each in 0.3×SSC, 0.1% SDS, always at a temperature of 55° C. The probe remained coupled to the homologous sequences on the membrane and was detected by autoradiography.

The RNA extracted from the young leaves of the Montebello and Nocchione varieties and from the kernels of the San Giovanni variety was separated on denaturing gel in the presence of formamide and transferred to nylon membrane by Northern blotting (Maniatis, Molecular cloning, 1989, Cold Spring Harbor Laboratory Press, 7.43–7.45). 40 µg/sample of total RNA extracted from San Giovanni kernels, Nocchione leaves and Montebello leaves were used. 60 pg of probe were used as a positive control. The RNA was loaded onto a 1% agarose gel in the presence of formaldehyde. The samples were then subjected to electrophoresis for 3 hours at 80 volts in the presence of 1×MOPS. The gel was rinsed in $H_2O$ and then stained with ethidium bromide 0.5 µg/ml to display the RNA. The RNA was then transferred onto a nylon membrane (Boehringer) by "capillary blotting" in the presence of 20×SSC throughout the night at 4° C. After transfer, the membrane was dried on 3 MM paper and then fixed by crosslinking using UV light (Stratagene UV Stratalinker 120000 µJ/cm$^2$). The RNA was hybridised with the Arabidopsis Δ12 desaturase probe as described for the DNA. Detection was carried out by autoradiography. The heterologous Arabidopsis probe was able to display a band with a molecular weight of about 1500 bp in the hazel RNA and 3 bands of about 18, 8 and 2.8 kb in the hazel DNA cut with Eco RI.

Construction of a Gene Library of cDNA

The gene library of cDNA was constructed from RNA from kernels harvested when almost fully ripe and taken from plants of the San Giovanni variety. For this purpose, the Poly(A)+mRNA was isolated from the total RNA with the use of the Poly(A)Tract mRNA Isolation System II, in accordance with the method provided by the firm Promega. The samples were eluted in $H_2O$ and precipitated with 0.1 volumes of 3M NaOAc and 3 volumes of 95% ethanol. After one night at −80° C., the RNA was centrifuged for 15' at 14000 rpm (Eppendorf), the pellet was rinsed in 75% ethanol and resuspended in 10 µl of $H_2O$. The concentration was read with a spectrophotometer and the yield was 3.2 µg of Poly(A)+mRNA per mg of total RNA.

The messenger RNA polyadenilate derived from kernels of the San Giovanni variety was used as a template for the synthesis of complementary DNA (cDNA) with the use of Boehringer's "cDNA synthesis kit" in accordance with the method recommended by the suppliers. An extraction was then carried out with one volume of phenol:chloroform:isoamyl alcohol (25:24:1). The cDNA was then purified in a Pharmacia column (cDNA spun columns) after the addition of NaCl 100 mM. The buffer used was the following: 10 mM Tris-HCl pH 7.5, 1 mM EDTA, 150 mM NaCl. Eco RI "adaptors" (Pharmacia) were added to the ends of the cDNA. The reaction mixture contained: 5 µl of cDNA (half of the cDNA obtained from 6 µg of Poly(A)+RNA), 10 µl of ligase buffer 10×(Promega), 10 µl of Eco RI adaptors (0.01 u/µl), 6 units of T4 DNA ligase (Promega), in a final volume of 100 µl. After incubation for 12 hours at 12° C., the ligase enzyme was inactivated for 10' at 65° C. Phosphorylation of the adaptors then followed by the addition, to the 100 µl mixture, of 10 µl of 100 mM ATP and 10 units of T4 polynucleotide kinase. After incubation at 37° C. for 30', the enzyme was inactivated by incubation for 10' at 65° C. Purification was then carried out with one volume of phenol:chloroform:isoamyl alcohol (25:24:1). The cDNA was then purified from fragments of less than 400 bp as follows. After the addition of NaCl to a final concentration of 0.1M NaCl, the cDNA was separated by chromatography in a column with Sepharose CL-4B resin (Size prep 400 spun column, Pharmacia) according to the method suggested by the suppliers. The fragments of cDNA shorter than 400 bases were thus excluded. The cDNA was precipitated with one thirtieth of a volume of 3M NaOAc and 2 volumes of 95% ethanol, centrifuged and resuspended in 10 µl of $H_2O$.

The cDNA was inserted in the λ phage vector Zap II cut with Eco RI and dephosphorylated (Stratagene) in the following manner: 2 µl of cDNA (200 ng), 1 µl of λ Zap II cut with Eco RI (1 µg/µl) (Stratagene), 0.5 µl of T4 DNA Ligase (4 U/µl) (Promega), 0.5 µl of 10×ligation buffer (Promega), 1 µl of $H_2O$. The reaction mixture was incubated for 14 hours at 12° C. The mixture containing the cDNA inserted in the vector was used for the reconstruction of the phages with the use of Stratagene's Gigapack Gold "in vitro packaging" kit. The gene library of phages thus obtained was constituted by about 300,000 pfu (plaque-forming units). In order to amplify the gene library, XL1 Blue MRF' cells were prepared as described by Stratagene and used the same day. The gene libraries were plated at a concentration of about 5000 pfu per plate (95 cm$^2$). After growth, the phages were resuspended in SM (5.8 gr/l NaCl, 2 gr/l $MgSO_4.7H_2O$, 50 ml/l 1M Tris HCl (pH 7.5), 5 ml/l 2% gelatine) and, after the addition of chloroform to 5% and incubation for 15 minutes at ambient temperature, the cell debris was centrifuged for 10 minutes at 2000×g. Chloroform to 0.3% was added to the supernatant liquid and the phages were preserved at 4° C. Aliquots were preserved at −70° C. after the addition of DMSO to 7%. The gene library was titled.

Construction of a Partial Genome Gene Library

The DNA of the Nocchione variety was digested with Eco RI restriction enzyme and separated on agarose gel. The fragments with lengths of up to 10000 bp (base pairs) were isolated from the gel with the use of Qiaex resin according to the Qiagen's method. For cloning in the λ vector Zap II, 400 ng of DNA fragments were incubated with 1 µg of desphosphorylated λ Zap II (Stratagene) in the presence of ligase buffer and 1.5 units of T4 DNA ligase (Promega) for 12 hours at 14° C.

Stratagene's Gigapack Gold "in vitro packaging" kit was used in accordance with the suppliers' instructions to make up the gene library. The gene library of phages thus produced was amplified as described for the cDNA gene library. The complexity of the gene library was 1,500,000 clones. This gene library was also amplified.

Screening of the cDNA Gene Library

About 250,000 phages of the cDNA gene library were plated on LB broth in the presence of XL1 Blue MRF' cells, divided into 12 plates each containing 20,000 pfu. After growth, the phages were transferred onto nylon membranes and their denatured DNA was fixed on the membranes as described by Boehringer for screening with non-radioactive probes. The membranes were then hybridized with the Arabidopsis Δ12 desaturase gene. The probe was prepared by the isolation of the insert containing the entire coding region of the gene from the plasmid. The insert was then marked with digoxigenin-dUTP with the use of Boehringer's "DNA labelling kit". Prehybridization was carried out in standard buffer (Boehringer) and hybridization was carried out in the same buffer with the addition of the Arabidopsis probe at a concentration of 10 ng/ml and at a temperature of 55° C.

After washing twice in 2×SSC, 0.1% SDS for 5 minutes at ambient temperature and washing twice in 0.3×SSC, 0.1%SDS at 55° C., detection was carried out with the use of an anti-digoxigenin antibody conjugated with alkaline phosphatase (Boehringer) and a chemiluminescent substrate (AMPPD, Boehringer).

11 positive phage plaques were identified. These were isolated, the phages resuspended in SM and titled. From 50 to 200 phages were plated for each positive plaque. The plaques were transferred onto nylon membranes and subjected to a second hybridization with the Arabidopsis Δ12 desaturase probe, as already described above. The following clones which could hybridize with the Arabidopsis Δ12 desaturase gene were obtained from the second screening: I, F, 4.

Screening of the Genome Gene Library

The gene library of Nocchione DNA was subjected to screening in the same way as the cDNA gene library. 1,600,000 phages were plated, divided into 40 plates. After growth, they were transferred to nylon membranes as described for the cDNA gene library. The membranes were then hybridized with the Arabidopsis Δ12 desaturase gene as described for the cDNA gene library. Autoradiography of the membranes showed 9 positive plaques. These plaques were isolated, titled and subjected to a second screening. 6 plaques were re-confirmed as positive. 4 of these gave a very strong signal.

Analysis of the Clones Isolated

The following positive phage clones were converted into plasmids by in vivo excision in accordance with the method suggested by Stratagene (Gigapack Gold in vitro packaging): I, F, 4 (cDNA gene library), N2, N11, N17, N18, N21, N25 (genome gene library).

Figure 1:
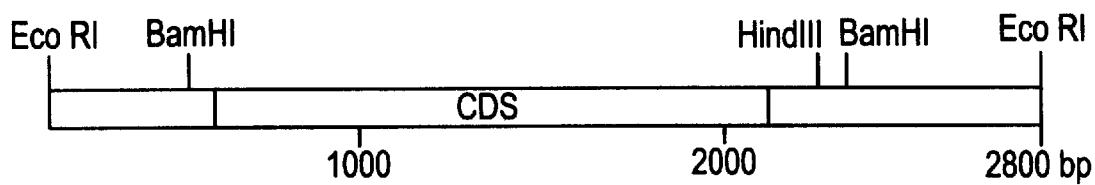
FIG. 1 shows the restriction map of the N2 genome clone.

The plasmid DNA of the clones of the cDNA gene library was isolated and the length of the insert analyzed by digestion with Eco RI. The plasmid DNA of the genome clones was isolated, the length of the insert analyzed by cutting with restriction enzyme, and the clones rechecked by hybridization with the Arabidopsis probe. FIG. 1 shows the map of the N2 genome clone.

Sequencing

The N2 clone was selected from the genome clones. For sequencing, the insert was fragmented with Sau3A restriction enzyme and the fragments obtained were subcloned in pUC18 vector cut with BamHI (Maniatis, Molecular cloning, 1989, Cold Spring Harbor Laboratory Press, 1.68–1.69). The clones obtained were analyzed both for the length of the insert and by hybridization with the Arabidopsis probe. Since the N2 insert was 2.8 kb and hence longer than the Δ12 desaturase gene, the hybridization excluded the clones containing sequences outside the gene. The insert of the I, F, 4 and N2 clones was isolated and sequenced with the use of the Sequenase kit and (35S)dATP. All of the clones (cDNA and genome) were first sequenced at the ends with the use of primers which could couple with the vector in both orientations. In order to complete the internal regions and to assemble the fragments of the N2 genome clone, internal oligonucleotides were then designed and synthesized and were used for the sequencing. The following table shows the sequences of the internal oligonucleotides: 1

| OLIGONUCLEOTIDE | SEQUENCE |
|---|---|
| N2-3SS (SEQ ID NO:6) | CAG ACC AGC ATC CGA GAC |
| N2-3SD (SEQ ID NO:7) | GGA TTG GCT TAG GGG GGC |
| N2-29R'S (SEQ ID NO:8) | GCC AAC CAT GTC ATC AAC CC |
| NOCCS (SEQ ID NO:9) | ATG GTA GAG AAG AGA TGG TG |
| COL (SEQ ID NO:10) | CTG GTG GGT TGT TGA AG |
| N2-S1N (SEQ ID NO:11) | GGA GAG GTC ATA AAC AAC |

0

The I and F clones were sequenced entirely. As far as the N2 clone is concerned, only the regions corresponding to the FAD2-N gene were sequenced. FIGS. 2 (SEQ ID NO:1) and 3 (SEQ ID NO:8) show their sequences. The I and F cDNA clones were identical. A comparison between the I (SEQ ID NO:3) and the N2 (SEQ ID NO:1) genome clone showed the same sequence (FIG. 4), indicating that N2 (SEQ ID NO:1) contains the gene which codes for the cDNA of the I clone (SEQ ID NO:3).

Comparison Between the Gene Isolated and Other Desaturases

The nucleotide and amino-acid sequence of the N2 clone (SEQ ID NO:1) was compared with other desaturases (FIG. 6). The greatest homology was with the two Δ12 desaturases of the endoplasmic reticulum of soya and Arabidopsis and with a hydroxylase of ricin which uses the same substrate as Δ12 desaturase. Homology with the plastid Δ12 desaturases and with both the plastid and endoplasmic reticulum Δ15 desaturases was, however, much lower. FIG. 5 shows the comparison between the amino acid sequence of hazel Δ12 desaturase and those sequences for Δ12 desaturase of Arabidopsis and soya.

Checking the Expression of the Hazel Δ12 Desaturase Gene

RNA was extracted from kernels of the San Giovanni, Montebello and Nocchione varieties and from leaves of the Montebello and Nocchione varieties. After separation on agarose gel, the RNA was transferred onto a nylon membrane and hybridized with the insert of the I clone marked with digoxigenin. The result is shown in FIG. 7, in which a band is visible in the kernel RNA but not in that of the leaves.

What is claimed is:

1. An isolated nucleic acid encoding hazel Δ12 desaturase, wherein said nucleic acid is DNA encoding the amino acid sequence set forth in SEQ ID NO. 2.

2. An isolated nucleic acid encoding the Δ12 desaturase according to claim 1, wherein said Δ12 desaturase comprises the same amino acid sequence as set forth in SEQ ID NO. 2.

3. An isolated nucleic acid encoding the Δ12 desaturase according to claim 2, wherein said Δ12 desaturase is of the endoplasmic reticulum.

4. An isolated nucleic acid from hazel comprising the nucleotide sequence as set forth in SEQ ID NO. 1 and encoding Δ12 desaturase.

5. An isolated nucleic acid from hazel comprising the nucleotide sequence as set forth in nucleotides 222–1367 of SEQ ID NO. 1 and encoding Δ12 desaturase.

6. A substantially purified hazel Δ12 desaturase enyzme of the endoplamsic reticulum having the amino acid sequence set forth in SEQ ID NO. 2.

7. A fusion polypeptide comprising the amino acid sequence of the enzyme of claim 6.

8. An isolated nucleic acid from hazel comprising the "I" clone cDNA (SEQ ID No: 3).

9. A process for the isolation of genes coding for enzymes having the function of hazel desaturase or of the desaturase of another species from genetic material, comprising: (1) hybridizing an isolated nucleic acid encoding hazel Δ12 desaturase according to claim 1 with said genetic material; and (2) detecting said genetic material coding for said enzymes.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 1662 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:1:

```
CCTCATAAAA AAGTAAGCTC ATTTACCTCA AGTAGGGTTT CCTTATGACA AATGAGTCCC      60
GCAATCCTTT TCTATGAGGT GCTATAATTG CAAATGTCCA AATCATAGGG ATATGGATCC     120
AAATACTATT AATATTATGT AGTGTGTTTT TTTTTTTCCC TCAAATTTAC TCTCACACCT     180
AAGTTGATTT TCTCCAGCAT TGGACATAGC CTCTGTAGAC AATGGGAGCT AGAAGCCGAA     240
TGCCTGCTAC CAACAAGCCT AAAGAGCAAA AACACCCAT CCAGCGAGCA CCACACACAA      300
AACCCCCATT CACTCTTAGC CAACTCAAGA AGCCGTCCC ACCCAATTGT TCCAACGCT       360
CTCTCCTACG CTCGTTCTCA TATGTTGTTT ATGACCTCTC CTTAGCCTTC CTCTTCTACT     420
ATATTGCTAC CTCTTACTTC CATCTCCTCC CTCACCCCCT TTCCTACTTG GCATGGTCAA     480
TCTATTGGGC TCTCCAAGGC TGCATTCTCA CCGGCGTTTG GGTCATCGCA CATGAGTGCG     540
GTCACCATGC CTTTAGTGAC TACCAATGGG TTGATGACAT GGTTGGCCTA ACCCTTCACT     600
CTGCTCTTTT AGTTCCATAC TTTTCATGGA AGATTAGCCA CTGTCGCCAC CACTCTAACA     660
CCGGCTCCCT TGACCGAGAT GAGGTGTTTG TCCCCAAGCC GAAATCCAAA ATGCCATGGT     720
TTTCTAAGTA CTTCAACAAC CCACCAGGTA GGGTCCTCAC TCTTTTGATC ACACTCACTC     780
TAGGCTGGCC CTTGTACTTA GCCTTGAATG TTTCTGGCCG ACCCTATGAT CGTTTTGCTT     840
GCCACTATGA TCCCTATGGC CCCATTTATT CCAATCGCGA AAGGTGTCAA ATATTTGTCT     900
CGGATGCTGG TGTCTTTGCT ACAACTTATG TGCTTTACTA CGCAGCAATG TCAAAAGGGC     960
TGGCATGGCT TGTATTCATT TATGGTATGC CATTGCTCAT AGTGAATGGC TTCCTTGTAT    1020
TAATCACCTA CTTGCAGCAC ACTCACCCTG CATTGCCGCA CTATGACTCA TCGAATGGGA    1080
TTGGCTTAGG GGGGCATTGG CGACGGCGGA TAGAGATTAC GGAATGCTGA ATAAGGTTTT    1140
CCACCAATAT CATAGACACC CATGTGGCTC ACCATCTCTT CTCTACCATG CCTCATTACC    1200
ATGCAATGGA AGCCACCAAA GCAATCAAGT CAATATTGGG CAAATACTAC CAGTTTGATG    1260
GCACTCCAGT TTACAAGGCA GTGTGGAGGG AGGCTAAAGA GTGCCTTTAT GTTGAGTCGG    1320
ACGAGGGGGC CCCTAACAAA GGTGTTTTCT GGTATCAGAG CAAGCTGTGA TATTGGCTGG    1380
ATAGAGCCAA AGAAAATGTG ATTAGTAAGG TAGTGTCTTT GGTCAGTTTG GTGTGTTAAG    1440
GAACAAATAA TAATAATTAG CGACTATGAA TAGTTATTGT TAAACAAAAT TCACCCTTAT    1500
GTTTAGCAGG AACTTTTCTG GCTACACTTT TTTTCGTATG AAAAGCGCAT ATTTTTTAAT    1560
TGTTATATTG TTTTGACATT ACTCAAGCTT CAAAATTAAT ATCACAGAAA ATATCCAATG    1620
TCGAAGGTTT CATTGTAGGT TGAAAACTTT ATATTGAGGT GG                       1662
```

(2) INFORMATION FOR SEQ ID NO:2:

(i) SEQUENCE CHARACTERISTICS:
        (A) LENGTH: 382 amino acids
        (B) TYPE: amino acid
        (C) STRANDEDNESS: single
        (D) TOPOLOGY: linear (xi) SEQUENCE DESCRIPTION: SEQ ID NO:2:

```
Met Gly Ala Arg Ser Arg Met Pro Ala Thr Asn Lys Pro Lys Glu Gln
 1               5                  10                  15

Lys Thr Pro Ile Gln Arg Ala Pro His Thr Lys Pro Pro Phe Thr Leu
            20                  25                  30

Ser Gln Leu Lys Lys Ala Val Pro Pro Asn Cys Phe Gln Arg Ser Leu
            35                  40                  45

Leu Arg Ser Phe Ser Tyr Val Tyr Asp Leu Ser Leu Ala Phe Leu
 50                  55                  60

Phe Tyr Tyr Ile Ala Thr Ser Tyr Phe His Leu Leu Pro His Pro Leu
 65                  70                  75                  80

Ser Tyr Leu Ala Trp Ser Ile Tyr Trp Ala Leu Gln Gly Cys Ile Leu
                85                  90                  95

Thr Gly Val Trp Val Ile Ala His Glu Cys Gly His His Ala Phe Ser
                100                 105                 110

Asp Tyr Gln Trp Val Asp Asp Met Val Gly Lys Thr Leu His Ser Ala
                115                 120                 125

Leu Leu Val Pro Tyr Phe Ser Trp Lys Ile Ser His Cys Arg His His
            130                 135                 140

Ser Asn Thr Gly Ser Leu Asp Arg Asp Glu Val Phe Val Pro Lys Pro
145                 150                 155                 160

Lys Ser Lys Met Pro Trp Phe Ser Lys Tyr Phe Asn Asn Pro Pro Gly
                165                 170                 175

Arg Val Leu Thr Leu Leu Ile Thr Leu Thr Leu Gly Trp Pro Leu Tyr
            180                 185                 190

Leu Ala Leu Asn Val Ser Gly Arg Pro Tyr Asp Arg Phe Ala Cys His
            195                 200                 205

Tyr Asp Pro Tyr Gly Pro Ile Tyr Ser Asn Arg Glu Arg Cys Gln Ile
        210                 215                 220

Phe Val Ser Asp Ala Gly Val Phe Ala Thr Thr Tyr Val Leu Tyr Tyr
225                 230                 235                 240

Ala Ala Met Ser Lys Gly Leu Ala Trp Leu Val Phe Ile Tyr Gly Met
                245                 250                 255

Pro Leu Leu Ile Val Asn Gly Phe Leu Val Leu Ile Thr Tyr Leu Gln
            260                 265                 270

His Thr His Pro Ala Leu Pro His Tyr Asp Ser Ser Glu Trp Asp Trp
        275                 280                 285

Leu Arg Gly Ala Leu Ala Thr Ala Asp Arg Asp Tyr Gly Met Leu Asn
        290                 295                 300

Lys Val Phe His Asn Ile Ile Asp Thr His Val Ala His His Leu Phe
305                 310                 315                 320

Ser Thr Met Pro His Tyr His Ala Met Glu Ala Thr Lys Ala Ile Lys
                325                 330                 335

Ser Ile Leu Gly Lys Tyr Tyr Gln Phe Asp Gly Thr Pro Val Tyr Lys
            340                 345                 350

Ala Val Trp Arg Glu Ala Lys Glu Cys Leu Tyr Val Glu Ser Asp Glu
            355                 360                 365

Gly Ala Pro Asn Lys Gly Val Phe Trp Tyr Gln Ser Lys Leu
        370                 375                 380

(2) INFORMATION FOR SEQ ID NO:3:

(i) SEQUENCE CHARACTERISTICS:
        (A) LENGTH: 1133 base pairs
        (B) TYPE: nucleic acid
```

(C) STRANDEDNESS: single
            (D) TOPOLOGY: linear (ii) MOLECULE TYPE: cDNA to mRNA (xi) SEQUENCE DESCRIPTION: SEQ ID NO:3:

```
TCCAACGCTC TCTCCTACGC TCGTTCTCAT ATGTTGTTTA TGACCTCTCC TTAGCCTTCC      60
TCTTCTACTA TATTGCTACC TCTTACTTCC ATCTCCTCCC TCACCCCCTT TCCTACTTGG     120
CATGGTCAAT CTATTGGGCT CTCCAAGGCT GCATTCTCAC CGGCGTTTGG GTCATCGCAC     180
ATGAGTGCGG TCACCATGCC TTTAGTGACT ACCAATGGGT TGATGACATG GTTGGCCTAA     240
CCCTTCACTC TGCTCTTTTA GTTCCATACT TTTCATGGAA GATTAGCCAC TGTCGCCACC     300
ACTCTAACAC CGGCTCCCTT GACCGAGATG AGGTGTTTGT CCCCAAGCCG AAATCCAAAA     360
TGCCATGGTT TTCTAAGTAC TTCAACAACC CACCAGGTAG GGTCCTCACT CTTTTGATCA     420
CACTCACTCT AGGCTGGCCC TTGTACTTAG CCTTGAATGT TTCTGGCCGA CCCTATGATC     480
GTTTTGCTTG CCACTATGAT CCCTATGGCC CCATTTATTC CAATCGCGAA AGGTGTCAAA     540
TATTTGTCTC GGATGCTGGT GTCTTTGCTA CAACTTATGT GCTTTACTAC GCAGCAATGT     600
CAAAAGGGCT GGCATGGCTT GTATTCATTT ATGGTATGCC ATTGCTCATA GTGAATGGCT     660
TCCTTGTATT AATCACCTAC TTGCAGCACA CTCACCCTGC ATTGCCGCAC TATGACTCAT     720
CAGAATGGGA TTGGCTTAGG GGGGCATTGG CGACGGCGGA TAGAGATTAC GGAATGCTGA     780
ATAAGGTTTT CCACAATATC ATAGACACCC ATGTGGCTCA CCATCTCTTC TCTACCATGC     840
CTCATTACCA TGCAATGGAA GCCACCAAAG CAATCAAGTC AATATTGGGC AAATACTACC     900
AGTTTGATGG CACTCCAGTT TACAAGGCAG TGTGGAGGGA GGCTAAAGAG TGCCTTTATG     960
TTGAGTCGGA CGAGGGGGCC CCTAACAAAG GTGTTTTCTG GTATCAGAGC AAGCTGTGAT    1020
ATTGGCTGGA TAGAGCCAAA GAAAATGTGA TTAGTAAGGT AGTGTCTTTG GTCAGTTTGG    1080
TGTGTTAAGG AACAAATAAT AATAATTAGC GACTATGAAT AGTTATTGTT AAA           1133
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

```
CTGAATTCCA GGTGGAAGAA TGCC                                             24
```

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:5:

```
AGGAATTCGA CAATTTCTTC ACCATCATGC                                       30
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear -continued (xi) SEQUENCE DESCRIPTION: SEQ ID NO:6:

CAGACCAGCA TCCGAGAC                                              18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

GGATTGGCTT AGGGGGGC                                              18

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

GCCAACCATG TCATCAACCC                                            20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

ATGGTAGAGA AGAGATGGTG                                            20

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:10:

CTGGTGGGTT GTTGAAG                                               17

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

GGAGAGGTCA TAAACAAC                                              18